United States Patent
Quintanilla

(10) Patent No.: US 6,402,684 B1
(45) Date of Patent: Jun. 11, 2002

(54) APPARATUS FOR MANAGING URINARY FLOW IN A HOST

(76) Inventor: Jaime Quintanilla, P.O. Box 293040, Kerrville, TX (US) 78029

( * ) Notice: Subject to any disclaimer, the term of this patent is extended or adjusted under 35 U.S.C. 154(b) by 0 days.

(21) Appl. No.: 09/523,547

(22) Filed: Mar. 10, 2000

(51) Int. Cl.$^7$ .............................. A61F 2/00; A61F 2/02
(52) U.S. Cl. ........................................ 600/29; 600/30
(58) Field of Search ...................... 600/29, 30; 4/144.3

(56) References Cited

U.S. PATENT DOCUMENTS

| | | | | |
|---|---|---|---|---|
| 4,850,963 A | * | 7/1989 | Sparks et al. | 600/29 |
| 5,894,608 A | * | 4/1999 | Birbara | 4/144.3 |
| 6,056,687 A | * | 5/2000 | Polyak et al. | 600/29 |

* cited by examiner

Primary Examiner—Eric F. Winakur
Assistant Examiner—Nikita R Veniaminov
(74) Attorney, Agent, or Firm—Royston, Rayzor, Vickery & Williams, L.L.P.

(57) ABSTRACT

An apparatus for managing urinary flow in a host and having normally closed and actuated open states; operating similar to properly functioning sphincter. The apparatus consists of a funnel, at least one fixing arrangement, a closure member, a motive member, and an external control member. In one embodiment, the funnel is adapted to be located inside a host's bladder and urethra and is adapted to be removably fixed in place by the fixing arrangements. A housing separates the motive member components from the external environment such as urinary tract tissue and fluids. In an alternate embodiment, the housing also separates the closure member from the external environment. The motive member is in communication with the closure member and both are positioned with respect to the funnel for changing the state of the apparatus from normally closed to actuated open and vice versa. The motive member is in communication with and responsive to an external control member to place the closure member in a position corresponding to the apparatus state input to the external control member by an operator. In another embodiment, the funnel is constructed of material such that it may be rolled with the motive member and closure member for implanting in the host.

14 Claims, 1 Drawing Sheet

APPARATUS FOR MANAGING URINARY FLOW IN A HOST

TECHNICAL FIELD

The present invention pertains to methods of treatment of the living body and apparatus used in treatment of abnormal conditions of the human body. More specifically, the present invention pertains to urinary incontinent management apparatus implanted within the body for managing the lack of urinary restraint.

BACKGROUND ART

Urinary incontinence (UI) is an abnormal condition of the living human body and refers to the involuntary loss of urine in sufficient amounts to be considered a social or health problem. Types of urinary incontinence include urge, stress, overflow, and functional UI.

According to the National Institute of Diabetes and Digestive and Kidney Diseases (NIDDK), at least 13,000,000 Americans, most of them women, will experience problems with UI. It is widely asserted that 50% of nursing home residents and 28%–33% of those senior citizens not under nursing home care experience UI. The NIDDK estimated that Americans spent about $27.8 billion on UI in 1995. Urinary incontinence can lead to secondary health problems such as skin irritation, ulceration, bladder infections, sleep disturbances, reduced sexual activity, and septicemias. These secondary problems increase a patient's disability and require additional treatment resources.

Apparatus and methods of treatment for urinary incontinence are known. Over-the-counter absorbent products, deodorants, disinfectants, and skin care products are somewhat effective at managing symptoms of UI, but do not address the underlying problem. Furthermore, managing incontinence using these products and methods can lower a patient's motivation to seek appropriate medical help. This possibility presents risk in that incontinence may be a symptom of more dangerous health problems, such as tumors of the brain, spinal cord, bladder, or prostate. Behavioral treatments for UI require patients to learn new behaviors, but work best with motivated patients willing to spend time and effort in making changes.

Medication is generally available only for treatment of urge UI. However, side effects such as blurred vision, severe dry mouth, and constipation are prevalent.

Various surgical procedures are used to treat UI. These include surgery to remove blockages, to inject collagen, to improve bladder neck position, to support or replace the function of severely weak pelvic muscles, to enlarge the bladder, and to implant catheters and other apparatus. U.S. Pat. No. 4,401,107 to Haber et al. and U.S. Pat. No. 4,551,862 to Haber each disclose a prosthetic sphincter surgically implanted around a waste elimination passage. U.S. Pat. No. 4,711,231 to Finegold et al. for a surgically-implantable prosthesis system requires use of a reservoir, pump, and fluids to control opening and closing of a waste elimination passage.

German Patent No. DE 3636-766-A to Lang discloses a duct containing one fixed and one rotatable perforated disk. Upon rotatable alignment of the perforations in each disk, the contents of a patient's bladder or bowels may be discharged. These procedures introduce the corresponding risks associated with surgery and subsequent apparatus malfunction.

Several single-use, non-surgical apparatus for treating UI are known. The urinary control insert is a single use, balloon-tipped cylinder typically smaller than a tampon and inserted into the urethra using an applicator. The balloon inflates within the bladder, holding the apparatus in place. The balloon must be deflated and apparatus removed to urinate. A single-use foam pad, having adhesive on one side, is known which may be applied to the urethra opening to mitigate unintentional discharge. Such single-use solutions can be expensive and require repeated attention.

In view of the above described deficiencies associated with the use of known devices and methods for managing urinary incontinence, the present invention has been developed to alleviate these drawbacks and provide further benefits to the user. These enhancements and benefits are described in greater detail hereinbelow with respect to several alternative embodiments of the present invention.

DISCLOSURE OF THE INVENTION

The present invention is an apparatus for managing urinary flow in a host. The apparatus, which operates similar to a properly functioning sphincter, has at least two (2) states, i.e., normally closed and actuated open states. The apparatus consists of a funnel, at least one fixing arrangement, a closure member, a motive member, and an external control member. In one embodiment, the funnel is adapted to be located inside a host's bladder and urethra and is adapted to be removably fixed in place by the fixing arrangements. A housing separates the motive member components from the external environment such as urinary tract tissue and fluids. In an alternate embodiment, the housing also separates the closure member from the external environment. The motive member is in communication with the closure member and both are positioned with respect to the funnel for changing the state of the apparatus from normally closed to actuated open and vice versa. The motive member is in communication with and responsive to an external control member to place the closure member in a position corresponding to the apparatus state input to the external control member by an operator. In another embodiment, the funnel is constructed of material such that it may be rolled with the motive member and closure member for implanting in the host.

The beneficial effects described above apply generally to the exemplary devices and mechanisms disclosed herein of the invention. The specific structures through which these benefits are delivered will be described in detail hereinbelow.

BRIEF DESCRIPTION OF THE DRAWINGS

The invention will now be described in greater detail in the following way of example only and with reference to the attached drawings, in which.

MODE(S) FOR CARRYING OUT THE INVENTION

Detailed embodiments of the present invention are disclosed herein; however, it is to be understood that the disclosed embodiments are merely exemplary of the invention that may be embodied in various and alternative forms. The figures are not necessarily to scale, some features may be exaggerated or minimized to show details of particular components. Therefore, specific structural and functional details disclosed herein are not to be interpreted as limiting, but merely as a basis for the claims and as a representative basis for teaching one skilled in the art to variously employ the present invention.

Figure 1:
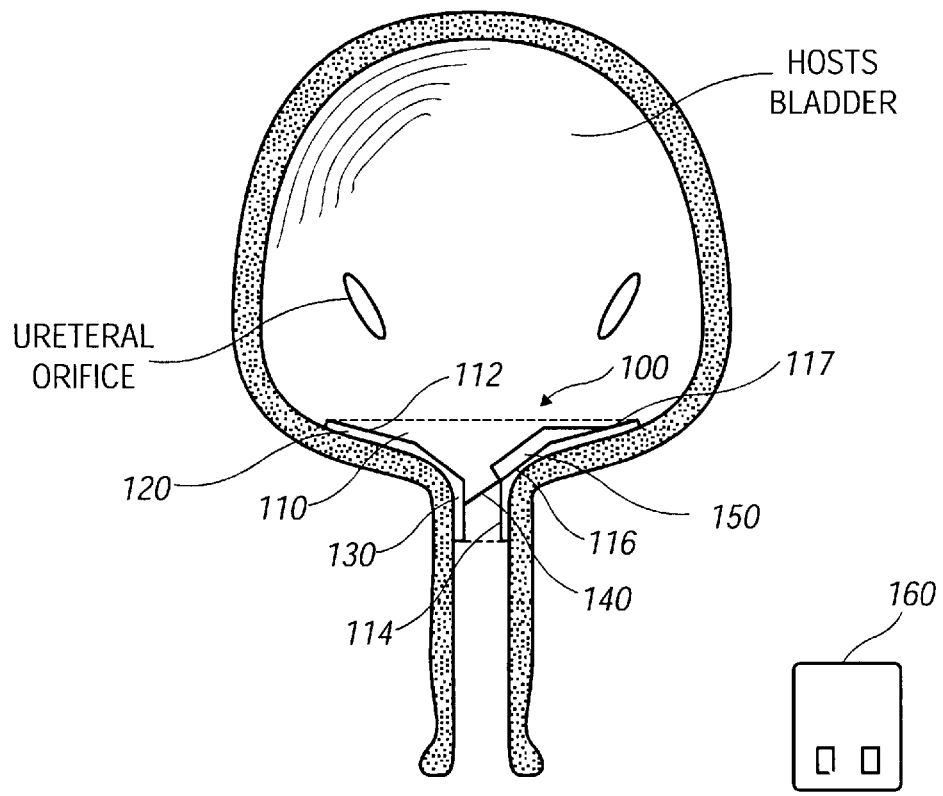
FIG. 1 is a schematic representation of a preferred embodiment of the present invention, an apparatus for managing urine incontinence as implanted in a urinary tract of a host.

Referring to FIG. 1, a schematic representation of a preferred embodiment of the present invention is shown, which is an apparatus for managing urinary incontinence 100. The normal state of the apparatus 100 is CLOSED. While in a CLOSED configuration, and when implanted in host, the apparatus 100 substantially prevents flow from the host's bladder, through the apparatus 100, and therefore into the host's urethra; similar to the effect of a properly functioning urinary sphincter. Upon actuation, the apparatus 100 changes state to an OPEN configuration. While OPEN, and when implanted in a host, the apparatus 100 substantially allows flow from the bladder, through the apparatus 100, and into the host's urethra; again similar to the effect of a properly functioning sphincter.

In the illustrated embodiment, the apparatus 100 consists of: a funnel 110; fixing arrangements 120, 130; a closure member 140; a motive member 150; and an external control member 160. In the illustrated embodiment, the funnel 110, closure member 140, and motive member 150 are adapted to be implanted in the host using the fixing arrangements 120, 130. The external control member 160 is adapted to be located external to the host.

In a preferred embodiment, the funnel 110 is made from a material compatible with the tissue and fluids found in a host's bladder and urethra. In use, the funnel upper portion 112 is located inside a host's bladder while the funnel lower portion 114 is located at the host's urethra. In the illustrated embodiment, the funnel upper portion 112 has two substantially conical sections of differing slope 116, 117. In other embodiments, the funnel upper portion 112 is substantially conformal with the interior surface of the host's bladder adjacent to the interface between the urethra and the bladder. Also in the illustrated embodiment, the funnel lower portion 114 is substantially cylindrical, but other tubular shapes are contemplated including a shape substantially conformal to the host's urethra.

In the preferred embodiment, the funnel 110 is fixed in place by the use of adhesives compatible with the tissue and fluids found in a host's bladder and urethra as the fixing arrangements 120, 130. Such adhesives used as fixing arrangements 120, 130 are placed between the exterior surface of the funnel upper portion 112 and the interior wall of a host's bladder and between the exterior surface of the funnel lower portion 114 and the interior wall of a host's urethra. Other fixing arrangements 120, 130 for fixing the funnel 110 in place include surgical implantation using sutures. In the illustrated embodiment, adhesives used as fixing arrangements 120, 130 are not permanent and may be removed or dissolved without any substantial permanent negative effect to the surrounding tissue. In a further embodiment, the same type of fixing arrangement is used to affix both the funnel lower portion 114 and upper portion 112 to the host's urethra and to interior wall of the host's bladder, respectively.

In the illustrated embodiment, the closure member 140 is a blade which is extended when the apparatus 100 is in the normally closed state and is retracted when the apparatus 100 is in the actuated open state. The blade 140, is oriented downward at an acute angle from an inlet rim of the funnel 110 in the illustrated embodiment so as not to impede evacuation of the host's bladder. In one embodiment, an inside wall of the funnel 110 is includes a grove to mate with the blade 140 to assure a good seal. In alternative embodiments, a closure element may be implemented using rotating disks, stationary/rotating ring combinations, or other artificial sphincter closure mechanisms known in the art, such as those identified as background art above.

Figure 2:
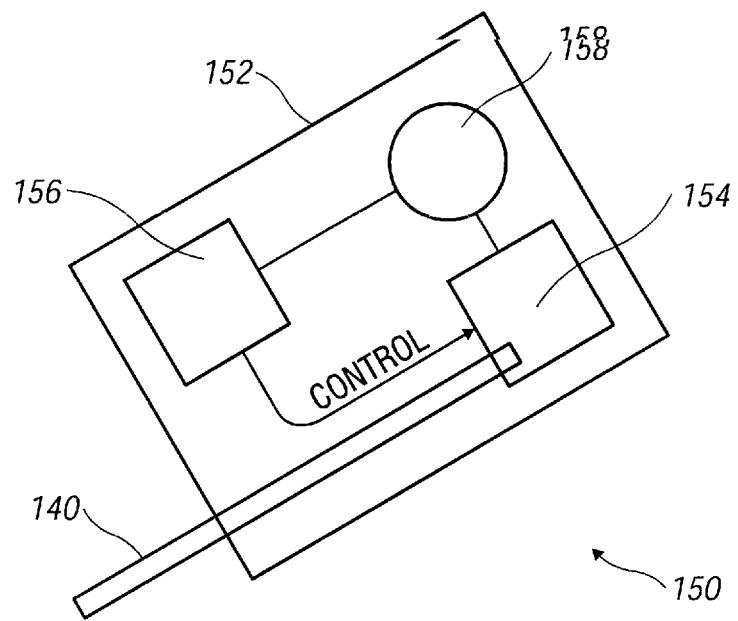
FIG. 2 is a schematic representation of a preferred embodiment of the motive member of the present invention.

In the preferred embodiment as shown in FIG. 2, the motive member 150 includes a motive member housing 152, prime mover 154, internal control member 156 and a power source 158. In the illustrated embodiment, the motive member 150 and closure member 140 are disposed inside the funnel 110. The motive member housing 152 separates the prime mover 154 and internal control member 156 from urinary tract tissue and fluids. In an alternative embodiment, the motive member housing 152 also separates the closure member 140 from urinary tract tissue and fluids. In that exemplary embodiment, the prime mover 154 is a micro motor. In alternative embodiments, the prime mover 154 may be any device which effectuates a change in the state of the closure member 140, for example, a magnet.

The power source 158 is in electrical communication with the prime mover 154 and internal control member 156 and is adapted to provide electrical power to those components for extended periods of operation. In a further embodiment the motive member power source 158 is be rechargeable without removal of the apparatus from the host.

The motive member prime mover 154 is in communication with the closure member 140 and both are positioned with respect to the funnel 110 for changing the state of the apparatus 100 from normally closed to actuated open and vice versa. In the illustrated embodiment, communication between the motive member prime mover 154 and the closure member 140 is mechanical; however, electromagnetic and similarly suited modes of communication are contemplated.

In the preferred embodiment, the external control member 160 is adapted to receive input from an operator to control the state of the apparatus 100. The external control member 160 is in electromagnetic or other suitable communication with the motive member 150. The motive member 150 is responsive to the external control member 160 to place the closure member 140 in a position corresponding to the apparatus state input by the operator.

In the illustrated embodiment, the funnel 110 is constructed of material such that it may be rolled with the motive member 150 and closure member 140 for implanting in the host.

An apparatus for managing urinary flow in a host been described herein. These and other variations, which will be appreciated by those skilled in the art, are within the intended scope of this invention as claimed below. As previously stated, detailed embodiments of the present invention are disclosed herein; however, it is to be understood that the disclosed embodiments are merely exemplary of the invention that may be embodied in various forms.

What is claimed and desired to be secured by Letters Patent is as follows:

1. An apparatus for managing urinary flow in a host and having mutually exclusive normally closed and actuated open states; said flow management apparatus comprising:
   a funnel comprising:
      an upper portion having an upper portion exterior surface, and
      a lower portion having a lower portion exterior surface;
   a first fixing arrangement adapted to affix said upper portion exterior surface to a host's bladder interior surface;

a second fixing arrangement adapted to affix said lower portion exterior surface to a host's urethra interior surface;

a closure member, operated by a motive member and an external control member that controls operation of said motive member;

said closure member:
  disposed and adapted to substantially prevent flow through said funnel when said flow management apparatus is in a normally closed state, and
  disposed and adapted to substantially allow flow through said funnel when said flow management apparatus is in an actuated open state;
  said external control member:
    adapted to receive input from an operator to control the state of said flow management device, and
  in electromagnetic communication with said motive member;
said motive member:
  in communication with said closure member, and
  responsive to said external control member to place said closure member in the state corresponding to the state of said flow management device input by the operator; and
a power source, said power source in electrical communication with and adapted to provide electrical power to said motive member.

2. The apparatus as recited in claim 1, wherein said closure member and said motive member are disposed within said funnel.

3. The apparatus as in claim 2, wherein said funnel is constructed from suitable material that permits said funnel to be rolled together with said motive member and said closure member for implantation in a host.

4. The apparatus as in claim 1, wherein said first fixing arrangement is a bio-compatible adhesive.

5. The apparatus as in claim 1, wherein said second fixing arrangement is a bio-compatible adhesive.

6. The apparatus as in claim 4, wherein said bio-compatible adhesive is dissolvable for later removal of apparatus from the host.

7. The apparatus as in claim 5, wherein said bio-compatible adhesive is dissolvable for later removal of apparatus.

8. The apparatus as in claim 1, wherein said closure member is a blade adapted for reciprocating motion.

9. The apparatus as in claim 8, wherein said funnel has an inlet rim and wherein said blade is oriented at an angle acutely downward from the inlet rim of said funnel in an upright host.

10. The apparatus as in claim 1, wherein said upper portion is substantially conical.

11. The apparatus as in claim 1, wherein said upper portion is adapted to substantially conform with an interior area of a bladder adjacent to the interface between the urethra and bladder.

12. The apparatus as in claim 1, wherein said lower portion is substantially cylindrical.

13. The apparatus as in claim 1, wherein said lower portion is adapted to substantially conform with an interior area of a urethra adjacent to an interface between the host's urethra and host's bladder.

14. An apparatus for managing urinary flow in a host and having mutually exclusive normally closed and actuated open states; said flow management apparatus comprising:
  a funnel comprising:
    an upper portion having an upper portion exterior surface, and
    a lower portion having a lower portion exterior surface;
  a fixing arrangement:
    adapted to affix said upper portion exterior surface to a host's bladder interior surface; and
    adapted to affix said lower portion exterior surface to a host's urethra interior surface;
  a closure member, operated by a motive member and an external control member that controls operation of said motive member;
  said closure member:
    disposed and adapted to substantially prevent flow through said funnel when said flow management apparatus is in a normally closed state, and
    disposed and adapted to substantially allow flow through said funnel when said flow management apparatus is in an actuated open state;
  said external control member:
    adapted to receive input from an operator to control the state of said flow management device, and
    in electromagnetic communication with said motive member;
  said motive member:
    in communication with said closure member, and
      responsive to said external control member to place said closure member in the state corresponding to the state of said flow management device input by the operator; and
  a power source, said power source in electrical communication with and adapted to provide electrical power to said motive member.

* * * * *